United States Patent [19]

Rasmussen

[11] 4,155,354

[45] May 22, 1979

[54] DISPOSABLE ELECTROMEDICAL ELECTRODE AND A SET OF SUCH ELECTRODES

[76] Inventor: Steen B. Rasmussen, No. 22 Birkholmvej, 3540 Uggelose Skov, Lynge, Denmark

[21] Appl. No.: 779,741

[22] Filed: Mar. 21, 1977

[30] Foreign Application Priority Data

Mar. 29, 1976 [DK] Denmark ............................. 1387/76

[51] Int. Cl.² .............................................. A61B 5/04
[52] U.S. Cl. ..................................... 128/640; 128/803
[58] Field of Search ............... 128/2.06 E, 2.1 E, 404, 128/416–418, DIG. 4

[56] References Cited

U.S. PATENT DOCUMENTS

| | | | |
|---|---|---|---|
| 2,943,628 | 7/1960 | Howell | 128/418 |
| 3,151,619 | 10/1964 | Sullivan | 128/417 |
| 3,505,993 | 4/1970 | Lewes et al. | 128/2.06 E |
| 3,620,208 | 11/1971 | Higley et al. | 128/2.06 E |
| 3,621,832 | 11/1971 | Fearnside et al. | 128/2.06 E |
| 3,720,209 | 3/1973 | Bolduc | 128/2.06 E |
| 3,746,004 | 6/1971 | Jankelson | 128/416 X |
| 3,774,592 | 11/1973 | Lahr | 128/2.1 E |
| 3,805,769 | 4/1974 | Sessions | 128/2.06 E |
| 3,826,246 | 7/1974 | Raddi et al. | 128/2.06 E |

FOREIGN PATENT DOCUMENTS

1363389  8/1974  United Kingdom ............... 128/2.06 E

*Primary Examiner*—Lee S. Cohen
*Attorney, Agent, or Firm*—Bacon & Thomas

[57] ABSTRACT

A disposable electromedical electrode comprises a supporting member including a dome-shaped central portion and a surrounding, annular and flat engagement portion as well as a connecting tab extending from the outer edge of the engagement portion and formed integrally with the supporting member. A continuous electrode coating is applied throughout the concave side of the central portion, the engagement portion and the connecting tab and is covered by an annular adhesive layer outside the engagement portion. The connecting tab is proportioned to allow direct and removable attachment of a connecting wire at a place spaced apart from the outer edge of the engagement portion. The electrode may be provided with a further electrode coating on the opposite side of the insulating supporting member to form a driven shield in use of the electrode. A number of electrodes may be supplied in a sheet- or strip-like electrode set incorporating a supporting layer of the same laminate configuration as the electrodes with fraction lines along the outer edges of the engagement portions and connecting tabs bent away from the supporting member to allow easy individual detachment of electrodes.

3 Claims, 5 Drawing Figures

DISPOSABLE ELECTROMEDICAL ELECTRODE AND A SET OF SUCH ELECTRODES

This invention relates to disposable electrodes for use in electromedical investigations, such as electroencefalography, electrocardiography and the like. In particular, the invention relates to a new and improved electrode construction, whereby disposable electrodes may be supplied in the form of an electrode set, from which the electrodes may be individually detached, and a method for manufacturing such an electrode set.

BACKGROUND OF THE INVENTION

In a widely used disposable electrode in the electromedical art, the contact member of the electrode is constituted by a separate, usually annular metallic member mounted on a flexible plaster-like support, which may either have been provided with an adhesive coating during manufacture, or onto which such an adhesive is supplied immediately prior to the use thereof.

On one hand, such an electrode construction is not very comfortable to the human skin due to the restriction of the engagement between the hard metallic member and the skin to the very small area of a circular arc, this small contact area giving also rise to difficulties in the provision of measuring signals which are sufficiently free of noise and disturbances. On the other hand, the manufacturing costs of such electrodes have appeared to assume such a level that the intended use as disposable electrodes is counteracted by economic considerations. In some cases, reuse of electrodes of this kind has been attempted by cleaning and washing, whereby the cost level will increase due to an increased load of work.

It has been suggested to make a cheaper disposable electrode, which is also more comfortable to the skin, by replacing the metallic contact member by contacting means of a textile material which has been made electrically conductive by carbonization or graphiting, such as disclosed in Danish Pat. No. 122,258. However, practice has shown that such electrodes suffer from severe problems with respect to suppression of noise and offset potentials. Therefore, these electrodes are not suitable for applications, in which more accurate measurements are required. Experiments have shown that the optimum electrical performance is still obtained by using metallic contact members, such as those of the silver/silver-chloride type.

From U.S. Pat. No. 3,151,619 a disposable electromedical electrode is known comprising a supporting member, the part of which intended for directly contacting the skin is constituted by an annular contact surface provided with an adhesive coating and surrounding a dome-shaped central portion, in which the contact member is provided in the form of a metallic electrode coating on the concave underside of this dome-shaped portion which defines a cavity for accommodation of an electrolytic paste.

Due to this construction of the electrode with a dome-shaped central portion which throughout the surface facing the skin carries a metallic electrode coating, a greater contacting surface is obtained, on one hand, so that noise may be efficiently suppressed, and a well defined cavity for the electrolytic paste is provided, on the other hand, whereby this paste or jelly will be prevented to some degree from leaking out of the electrode, which has appeared to be a disadvantage in known electrodes having a flat support which does not allow restricted localization of the paste or jelly.

SUMMARY OF THE INVENTION

It is the object of the invention to provide a further improvement of the latter prior art electrode construction, whereby electrolytic paste which may still leak out of the electrode between the annular engagement portion thereof and the skin will be substantially prevented from exerting any adverse influence at the place of contact between the connecting tab and the connecting wire.

According to the invention, there is provided a disposable electromedical electrode, comprising a supporting member of a flexible insulating material, said supporting member forming a dome-shaped central portion defining a cavity for accommodating an electrolytic paste and a surrounding annular and substantially flat skin-contacting portion, a connecting tab extending from the outer edge of said surrounding portion and being formed integrally with said supporting member, said connecting tab being porportioned to allow an attachment member of a connecting wire to be directly and removably attached to an extreme end of said tab spaced apart from the outer edge of said surrounding portion of the supporting member in the radial as well as the axial direction thereof, a continuous metallic electrode coating applied throughout the supporting member and the connecting tab to the surface thereof incorporating the concave side of said dome-shaped portion, and an insulating adhesive layer applied to the part of said electrode coating only, which covers said surrounding portion of the supporting member, whereby to be confined to an annular closed path and expose the electrode coating on said central portion and said connecting tab for contacting said electrolytic paste and said connecting wire, respectively.

Furthermore, the invention relates to a set of disposable electromedical electrodes of the above mentioned kind, in which said electrodes are supported in laterally spaced relationship by a supporting layer consisting of the same material as and formed integrally with the supporting member of each electrode, said material being partly removed along the outer edge of said surrounding portion of the supporting member of each electrode to allow individual detachment of the electrodes from the supporting layer, and a protective layer of a siliconized material is applied to the side of the supporting layer incorporating the adhesive layer of each electrode, the connecting tab of each electrode being bent away from the supporting layer to the opposite side thereof relative to said protective layer, so as to form an angle with said supporting layer.

By supplying the electrodes to the users, such as hospitals and the like, in the form of such electrode sets, the human work in connection with electromedical investigations will be facilitated, since the electrodes may be detached directly from the electrode set with an adhesive applied right from the beginning to the annular engagement portion for adhering to the skin, after which an electrical connecting wire may be attached directly to the connecting tab in a simple manner, for example, by means of a suitable clamp.

Moreover, the essential advantage is obtained that offsetpotentials between a reference electrode and an active electrode by electromedical investigations following from small differences in the electrode metal composition will be substantially avoided in practice, if the two electrodes are detached from one and the same electrode set, for instance as neighbour electrodes.

Practice has shown that in case of silver/silver-chloride as electrode metal, the price of electrodes manufactured by the method according to the invention will be lower than half the price of known electrodes.

BRIEF DESCRIPTION OF THE DRAWINGS

In the following the invention will be further explained with reference to the accompanying drawings, in which

As shown in FIG. 1, a disposable electrode of the kind dealt with herein comprises a supporting member having a mainly annular engagement portion 1 intended for directly contacting the skin and being provided, as explained in the following, with an adhesive on its underside, said engagement portion surrounding a dome-shaped central portion 2. From the outer edge of the annular engagement portion 1 there extends a connecting tab 3 for attachment of an electrical connecting wire 4 by means of, for example, a suitable attachment member as shown at 5.

Figure 2:
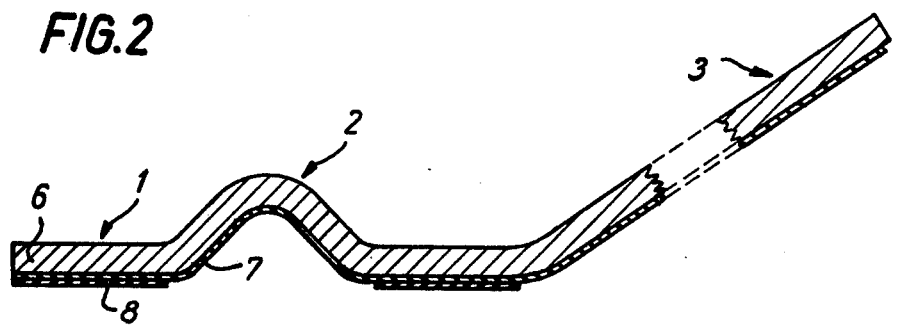
FIG. 2 is an enlarged sectional view of the electrode shown in FIG. 1.

The detailed construction of the electrode will appear from the enlarged sectional view in FIG. 2, in which the supporting member incorporating the annular engagement portion 1, the dome-shaped central portion 2 and the connecting tab 3 as integral parts are designated as a whole by 6. In order to allow the annular engagement portion 1 to be applied in direct contact with the skin in a comfortable manner, the supporting member 6 is made of a flexible insulating material, which may preferably be a semi-soft thermo-plastic material, such as ABS-plastic. An electrical contact member is provided on the concave underside of the dome-shaped central portion 2 in the form of a coating 7 of an electrode metal, which may preferably be silver/silver-chloride. According to the invention, the metallic electrode coating extends continuous throughout the underside of the supporting member 6 including the annular engagement portion 1, the dome-shaped central portion 2 and the connecting tab 3. However, the coating 7 is only exposed for electrical contacting purposes on the underside of the dome-shaped central portion 2 and the underside of the connecting tab 3, the electrode coating on the annular engagement portion 1 being covered by an electrically insulating adhesive layer 8 of a suitable adhesive not irritating the skin, which may be of the same type, for example, as used in ordinary plasters.

Figure 1:
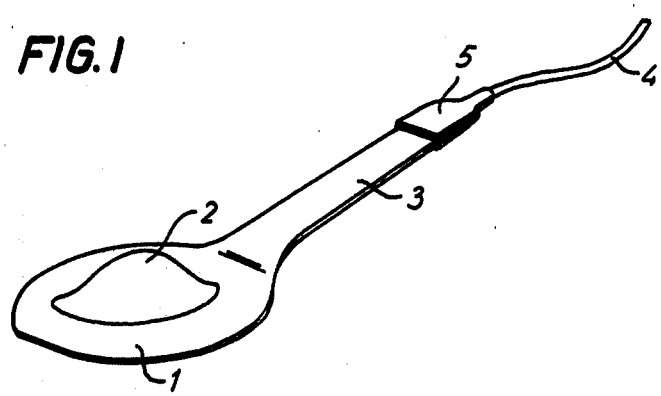
FIG. 1 is a perspective view of an embodiment of a single disposable electrode according to the invention.
Figure 3:
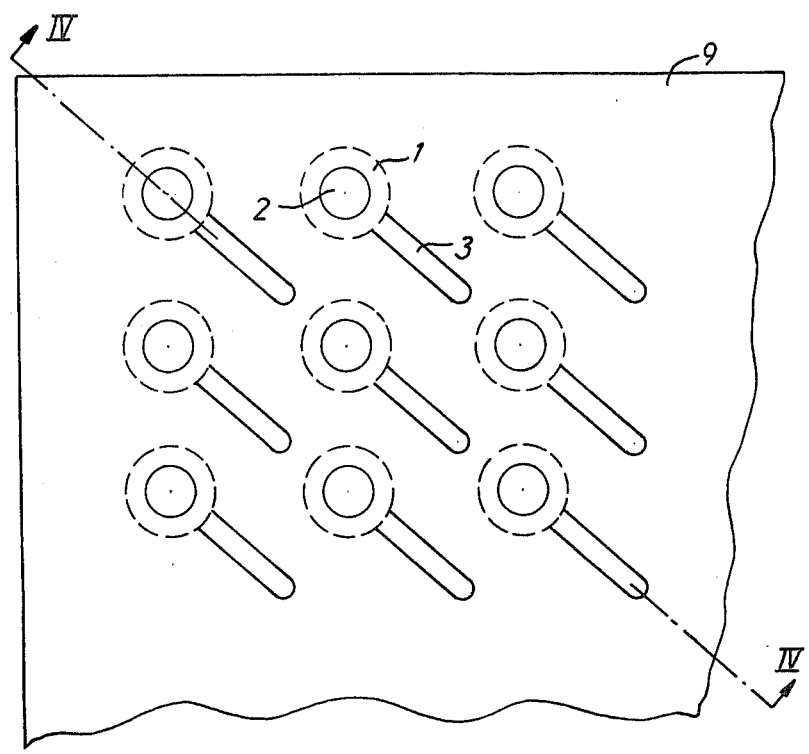
FIG. 3 is a plane view of a set of electrodes as shown in FIGS. 1 and 2 arranged on a sheet-like supporting layer.

In FIG. 3 a set of electrodes of the construction shown in FIGS. 1 and 2 is shown to be arranged on a sheet-like supporting layer 9. As mentioned in the following explanation of an embodiment of the method according to the invention, the supporting layer 9 between the individual electrodes consists of the same laminate configuration incorporating layers 6, 7 and 8 as the engagement portions 1 of the individual electrodes, while on the underside of the adhesive layer 8 there is provided in a manner known per se a protective layer of a siliconized material, such as paper or plastic. The supporting layer 9 may also have the form of a strip including a single row of electrodes.

By supplying disposable electrodes according to the invention to the users in the form of such an electrode set, in which only part of the annular engagement portion 1 of each electrode is connected with the surrounding material in the supporting layer 9, a particularly easy operation of the electrodes is obtained, since individual electrodes may easily be torn from the supporting layer 9, whereby they are provided right from the beginning with an adhesive on the annular engagement portion 1 to be directly applied to the desired points of measurement of the patient to be investigated. Thereafter, electrical connecting wires may easily be attached to the connecting tabs 3 of the individual electrodes.

As a result of the construction of the electrode incorporating the dome-shaped central portion 2, a well-defined cavity will be formed when the electrode is arranged with the annular engagement portion 1 in direct contact with the skin for applying an electrolytic paste of the kind used in electromedical measurements. The electrolytic paste may be introduced in this cavity, for example, by means of a syringe, the needle of which may be injected through the dome-shaped central portion 2 after arrangement of the electrode. Thereby, application of the electrolytic paste before the arrangement of the electrode will be avoided, and the electrolytic paste will be subject to restricted localization to the well-defined cavity under the central portion of the electrode, whereby it will be substantially prevented from leaking out of the electrode, which has appeared to be a frequent problem in case of known electrodes having totally flat electrode supports.

Furthermore, due to the particular proportioning of the connecting tab 3, the place of contact between the electrode metal proper and the electrical connection wire which is usually made of copper will be spaced apart from the zone of the electrolytic paste and will, therefore, not be exposed to galvanic influences therefrom.

In the following, an embodiment of a method according to the invention for manufacturing a set of disposable electrodes as shown in FIG. 3 at low costs will be explained with reference to the steps of manufacture illustrated by the sectional views in FIG. 4a-d. In these views, the thickness ratio of the individual layers of the electrodes has been distorted for the sake of clearness in the same manner as in the enlarged sectional view in FIG. 2. The starting material is the supporting layer 9, shown in FIG. 3, which may, as mentioned, consist of a flexible insulating material, preferably a semi-soft thermoplastic material, such as an ABS-plastic, and may have a thickness of e.g. 0.2 mms. In this supporting layer 9, the dome-shaped central portions 2 of the supporting members of the individual electrodes may be formed by a heat-stamping process, by which operation fraction lines may also be formed at the outer edges of the annular engagement portions 1 in such a way, for example by perforation, that at least part of the annular engagement portion 1 at each electrode is connected with the surrounding material in the supporting layer 9. Furthermore, fraction lines are formed at the outer edges of the connecting tab 3, and these tabs are bent, after which the supporting layer 9 will take the form shown in FIG. 4a.

Figure 4:
FIG. 4a-d are sectional views along the line IV—IV in FIG. 3 for illustration of the electrode set under various steps of manufacture by an embodiment of the method according to the invention, and FIG. 5 an enlarged cross-sectional view of a modification of the electrode shown in FIG. 2.
Figure 4:
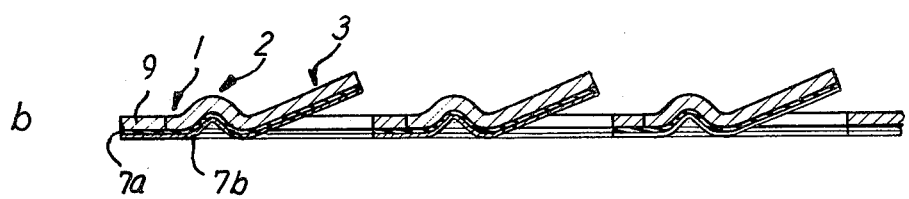
Figure 4:
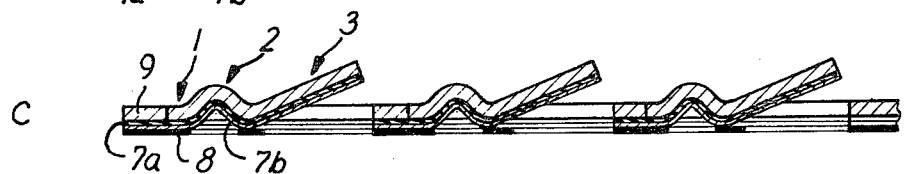
Figure 4:
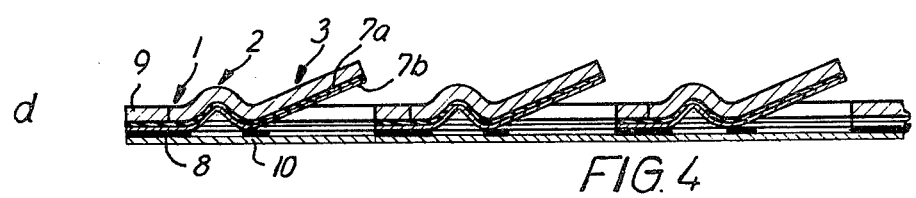

However, this method for producing the common supporting layer incorporating the electrode supporting members with dome-shaped central portions and bent connecting tabs is not limiting to the invention, since the configuration of the supporting layer 9 shown in FIG. 4a may also be obtained in one operation by injection moulding.

In the example shown, there is then applied to the underside of the supporting layer 9 thus formed, first a silver coating 7a which may be done by a galvanic process and, thereafter, a silver-chloride coating 7b which may be done by immersion in a silver-chloride bath. These coatings of silver and silver-chloride, which are applied throughout the underside of the supporting layer including the dome-shaped central portions 2 and the bent connecting tabs 3, such as shown in FIG. 4b, constitute together the metallic electrode coating 7, shown in FIG. 2, and are preferred as electrode materials, because they give optimum electrical performance with respect to the suppression of noice, as already mentioned in the foregoing. However, this choice of electrode material is not limiting to the method according to the invention, which could also be utilized with other electrode metals, which are suitable for being applied to a supporting layer of a plastic material by known metallization processes. After the application of electrode metal, there is applied, as shown in FIG. 4c, the adhesive layer 8 which at the annular engagement portion 1 shall provide electrical insulation between the metallic electrode coating 7 and the underlying skin. Preferably, an adhesive comfortable to the skin is used, which may, for example, be of the same type as used in ordinary plasters. The adhesive layer 8 is applied in such a way that the dome-shaped central portions 2 and connecting tabs 3 of the electrodes are not coated by the adhesive, said application taking place, for instance, by means of a cushion moistured with the adhesive in question.

Finally, a protective layer 10 is applied in known manner to the adhesive layer 8, said protective layer being of a siliconized material, such as plastic or paper in sheet form, whereby the finished electrode set will have a configuration as schematically shown in FIG. 4d.

However, the embodiment described above is not limiting to the method according to the invention, since in practice it will be possible and often preferable to interchange the first manufacturing steps, so that the supporting layer 9 is first in a flat condition provided with the electrode metal layers in the form of the silver coating 7a and the silver chloride coating 7b before the dome-shaped central portions and connecting tabs of the individual electrodes are formed together with fraction lines by heat stamping.

Figure 5:
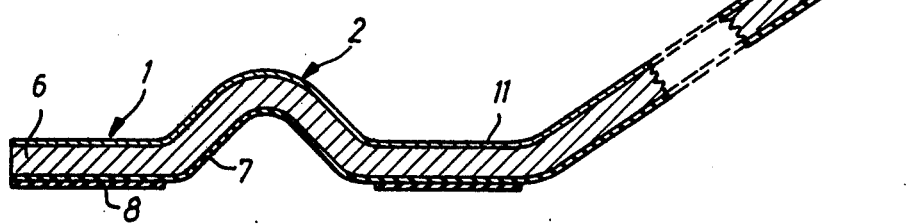

In FIG. 5, a modification of the disposable electrode according to the invention is shown, by which a particularly high degree of security against electrostatic disturbances has been obtained by means of a shield in the form of a further metallic electrode coating 11 throughout the upper side of the supporting member including the central portion 2, the engagement portion 1 and the connecting tab 3 of the electrode.

In use of this electrode, the active electrode coating 7 and the shield coating 11 are connected through conductors 12 and 13, respectively, of a twin-conductor connecting wire, such as a coaxial cable to individual inputs of an operational amplifier functioning as a voltage follower and comprising, for example, an insulated-gate field effect transistor in order to obtain a very high input impedance and a very low output impedance resulting in an impedance transformation from the active electrode coating 7 to the shield coating 11.

Thereby, a so-called driven shield is obtained, so that electrostatic disturbances of the desired measuring signals are eliminated, because the signal transmission takes place through shielded connections right from the place of contact between the electrode and the electrolytic paste onto the recording apparatus.

In the manufacture of a set of electrodes as shown in FIG. 5, the same method as explained in the foregoing may, in principle, be utilized, the further metallic electrode coating 11 being applied in the same process step as the active coating 7.

What is claimed is:

1. A disposable electromedical electrode, particularly for deriving measuring signals from the skin, comprising a supporting member of a flexible insulating material, said supporting member forming a dome-shaped central portion defining a cavity for accommodating an electrolytic paste and a surrounding annular and substantially flat skin-contacting portion, a connecting tab extending radially outward and axially upward from the outer edge of said surrounding portion and being formed integrally with said supporting member, said connecting tab being proportioned to allow an attachment member of a connecting wire to be directly and removably attached to an extreme end of said tab at such a separation from the outer edge of said surrounding portion of the supporting member in the radial as well as the axial direction thereof that contamination of the region of attachment by electrolytic paste leaking out of said central portion under said surrounding portion is avoided, a continuous metallic electrode coating applied throughout the supporting member and the connecting tab to the surface thereof incorporating the concave side of said dome-shaped portion, and an insulating adhesive layer applied to the part of said electrode coating only, which covers said surrounding portion of the supporting member, whereby to be confined to an annular closed path and expose the electrode coating on said central portion and said connecting tab for contacting said electrolytic paste and said connecting wiere, respectively.

2. A disposable electromedical electrode as claimed in claim 1, wherein a further metallic electrode coating is applied throughout the supporting member and the connecting tab to the surface thereof incorporating the convex side of said dome-shaped portion, whereby to provide a driven shield in use of the electrode.

3. A set of disposable electromedical electrodes, particularly for deriving measuring signals from the skin, comprising a plurality of electrodes, each electrode comprising a supporting member of a flexible insulating material, said supporting member forming a dome-shaped central portion defining a cavity for accommodating an electrolytic paste and a surrounding annular and substantially flat skin-contacting portion, a connecting tab extending radially outward and axially upward from the outer edge of said surrounding portion and being formed integrally with said supporting member, said connecting tab being proportioned to allow an attachment member of a connecting wire to be directly and removably attached to an extreme end of said tab at such a separation from the outer edge of said surrounding portion of the supporting member in the radial as well as the axial direction thereof that contamination of the region of attachment by electrolytic paste leaking out of said central portion under said surrounding portion is avoided, a continuous metallic electrode coating applied throughout the supporting member and the connecting tab to the surface thereof incorporating the concave side of said dome-shaped portion, and an insulating adhesive layer applied to the part of said electrode coating only, which covers said surrounding portion of the supporting member, whereby to be confined to an annular closed path and expose the electrode coating on said central portion and said connecting tab for contacting said electrolytic paste and said connecting wire, respectively, a supporting layer consisting of the same material as and formed integrally with the supporting member of each electrode and supporting said electrodes in a laterally spaced relationship, said material being partly removed along the outer edge of said surrounding portion of the supporting member of each electrode to allow individual detachment of the electrodes from the supporting layer, and a protective layer of a siliconized material applied to the side of the supporting layer facing in the same direction as the surface of the supporting member incorporating the concave side of the dome-shaped portion and covering the adhesive layer of each electrode, the connecting tab of each electrode being bent away from the supporting layer to the opposite side thereof relative to said protective layer so as to form an angle with said supporting layer.

* * * * *